United States Patent [19]

Theeuwes et al.

[11] 4,298,003
[45] Nov. 3, 1981

[54] SYSTEM FOR DELIVERING AGENT AT ZERO ORDER RATE WITH EMERGING AGENT BELOW SATURATION

[75] Inventors: Felix Theeuwes, Los Altos; Richard Cortese, San Jose, both of Calif.

[73] Assignee: ALZA Corporation, Palo Alto, Calif.

[21] Appl. No.: 149,020

[22] Filed: May 12, 1980

[51] Int. Cl.³ .............................................. A61M 7/00
[52] U.S. Cl. ................................................... 128/260
[58] Field of Search ....................... 128/127, 130, 260; 424/21–22

[56] References Cited

U.S. PATENT DOCUMENTS

| | | | |
|---|---|---|---|
| 3,732,865 | 5/1973 | Higuchi et al. | 128/260 |
| 3,995,632 | 12/1976 | Nakano et al. | 128/260 |
| 4,160,452 | 7/1979 | Theeuwes | 128/260 |
| 4,217,898 | 8/1980 | Theeuwes | 128/260 |
| 4,229,428 | 10/1980 | Cherqui et al. | 424/21 |

Primary Examiner—C. Fred Rosenbaum
Attorney, Agent, or Firm—Paul L. Sabatine; Edward L. Mandell

[57] ABSTRACT

An osmotic system is disclosed for delivering an agent. The system comprises a semipermeable wall surrounding a compartment. The compartment contains a layer of a compound that is insoluble in an exterior fluid, and juxtaposed with a layer of an agent that is soluble in the fluid. A passageway through the wall connects the exterior of the system with the interface between the wall and the insoluble compound. In operation, agent is delivered from the system, by the agent imbibing fluid into the compartment to form a saturated solution of agent, that is moved along the interface between the wall and the insoluble compound towards the passageway. The saturated solution is moved continuously by the corresponding imbibition of fluid, and as the solution moves along the interface it imbibs fluid, is diluted and delivered below a saturated concentration to the exterior of the system. The invention also concerns a two layered structure comprising a layer of an aqueous insoluble compound and a layer of an aqueous soluble compound.

15 Claims, 6 Drawing Figures

FIG.1
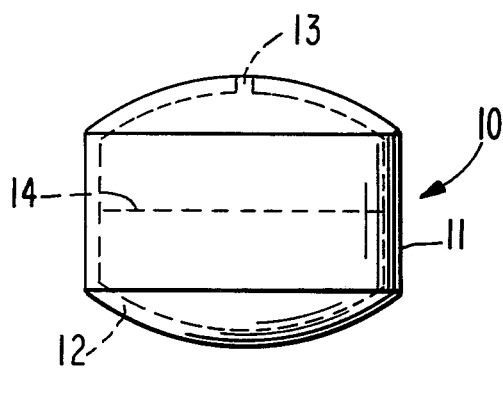
FIG.2
FIG.3
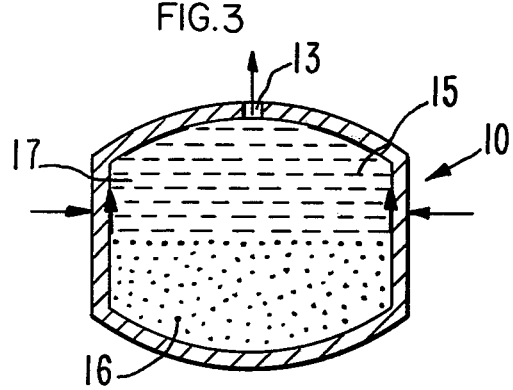
FIG.4
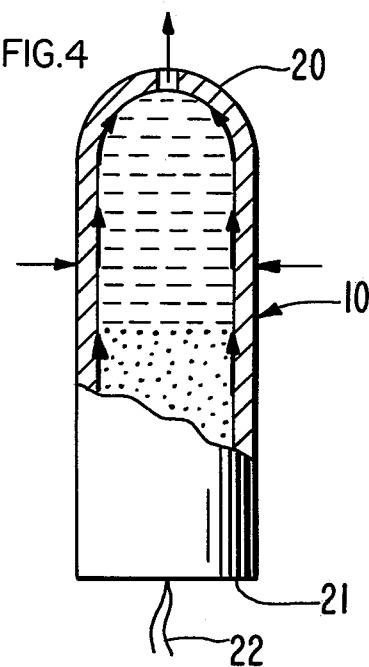
FIG.5
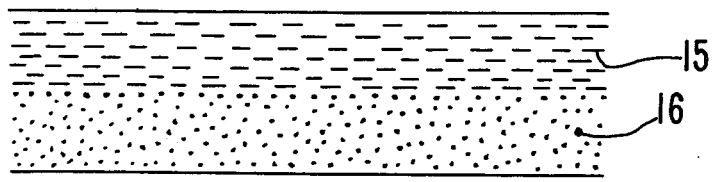

SYSTEM FOR DELIVERING AGENT AT ZERO ORDER RATE WITH EMERGING AGENT BELOW SATURATION

FIELD OF THE INVENTION

This invention pertains to an osmotic system manufactured in the form of an osmotic device. More particularly, the invention relates to an osmotic device for dispensing beneficial agents, that also can adversely affect an environment of use. Specifically, the invention concerns an osmotic system that can deliver a beneificial agent in solution below saturation, thereby obtaining the benefits of its useful activity, while lessening its incidence of adverse affect on the environment of use.

BACKGROUND OF THE INVENTION

There are many agents that are used for producing a beneficial effect that have serious shortcomings associated with their use. Many of these agents are drugs known to pharmacentical science. For example, the electrolyte potassium chloride is the salt most frequently used when the action of the potassium cation is desired for an indicated therapeutic effect. Potassium chloride is used when hypokalemia exists, as a treatment with certain diuretics, in steroid therapy, and for relieving the symptoms of Menier's disease. However, serious shortcomings are associated with its uses, mainly concentrated preparations of potassium chloride are an irritant to the gastrointestinal tract, and its use often leads to bowel lesions. Another important agent-drug that possesses similar shortcomings is aspirin. Aspirin, or acetalsalicylic acid, is widely used as an antipyretic and analygetic in a variety of medical conditions. Aspirin is a very potent drug; however, occult gastrointestinal bleeding often follows the use of conventional, concentrated dosage forms of the drug. One additional example of a useful drug whose usefulness often is compromised by unwanted effects is indomethacin. Indomethacin is a nonsteroidal indole that exhibits both analgesic and anti-inflammatory properties, and it is used most for the treatment of rheumatoid arthritis. The most frequent untoward actions associated with concentrated dosage forms containing this drug are gastrointestinal disturbances similar to those mentioned above.

The prior art has provided novel osmotic therapeutic systems manufactured in the form of osmotic devices for the precision administration of drugs with control of delivery patterns and with extended operational delivery times. Those systems are known in U.S. Pat. Nos. 3,845,770 and 3,916,899, both issued to patentees Felix Theeuwes and Takeru Higuchi. The patents are assigned to the ALZA Corporation of Palo Alto, Calif. The systems disclosed in these patents are made of a semi-permeable wall that surrounds a reservoir containing a drug. The systems disclosed in these patents are extraordinarily effective for delivering all kinds of drugs in the form of saturated solution over time. While the above systems represent an outstanding and pioneering advancement in the delivery art, and while they are useful for dispensing innumerable drugs to the biological environment of use, there is an occasional instance when a less than saturated solution is needed for a therapeutic indication. These instances are exemplified by the above mentioned prior art. Thus, in the light of this presentation, it will be appreciated by those versed in the dispensing art that if a system is made available for dispensing beneficial agents, including drugs, that dispenses the agents in less than concentrated amounts, such systems would have a definite use and represent a valuable contribution to the art.

OBJECTS OF THE INVENTION

Accordingly, it is an immediate object of this invention to provide an osmotic system that contributes to the prior art by making available a system that can be used for dispensing a beneficial agent in less than concentrated amounts to an environment of use.

Another object of the present invention is to provide an improvement in drug delivery by making available an osmotic device for the controlled and continuous delivery of a beneficial drug in a diluted amount over a prolonged period of time.

Yet another object of the invention is to provide as osmotic device consisting of a single compartment that houses a layer of an insoluble compound and a layer of a soluble useful agent, which device delivers the agent in solution below saturation amounts of the drug.

Still another object of this invention is to provide an osmotic device having a semipermeable wall with a passageway therethrough that connects the exterior of the device with the interfaced boundary between the inside of the wall and a layer of insoluble compound present in the device.

Still another object of this invention is to provide an osmotic device that in operation in situ can significantly reduce the high concentration of a drug solution to a more dilute solution, which diluted solution has a correspondingly decreased ability to produce injury to the tissues of the gastrointestinal tract.

Yet still a further object of the invention is to provide a two layered structure useful for manufacturing an osmotic delivery device.

Other objects, features, aspects and advantages of the invention will be more apparent to those versed in the art from the following detailed specification taken in conjunction with the figures and the accompanying claims.

BRIEF DESCRIPTION OF THE DRAWINGS

In the drawings, which are not drawn to scale, but are set forth to illustrate various embodiments of the invention, the figures are as follows:

FIG. 1 is a view of an osmotic system manufactured as an osmotic device designed for orally administering a beneficial drug to a warm-blooded animal;

FIG. 2 is an opened view of the device of FIG. 1 depicting the inside compartment of the device and the layered structured arrangement of the insoluble compound and the agent in the device;

FIG. 3 is an opened view of the device of FIG. 1 illustrating the device in operation delivering an agent from the device.

FIG. 4 illustrated a device with part of its semipermeable wall removed for viewing a device designed for dispensing a drug in a body opening such as the vagina or the ano-rectal channel;

FIG. 5 is an illustration of the two layered structure provided by the invention; and, FIG. 6 is a graph illustrating the dilution of a solution delivered from the osmotic system of the invention as a function of the pumping capacity of the diluting member.

In the drawings and the specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 6:
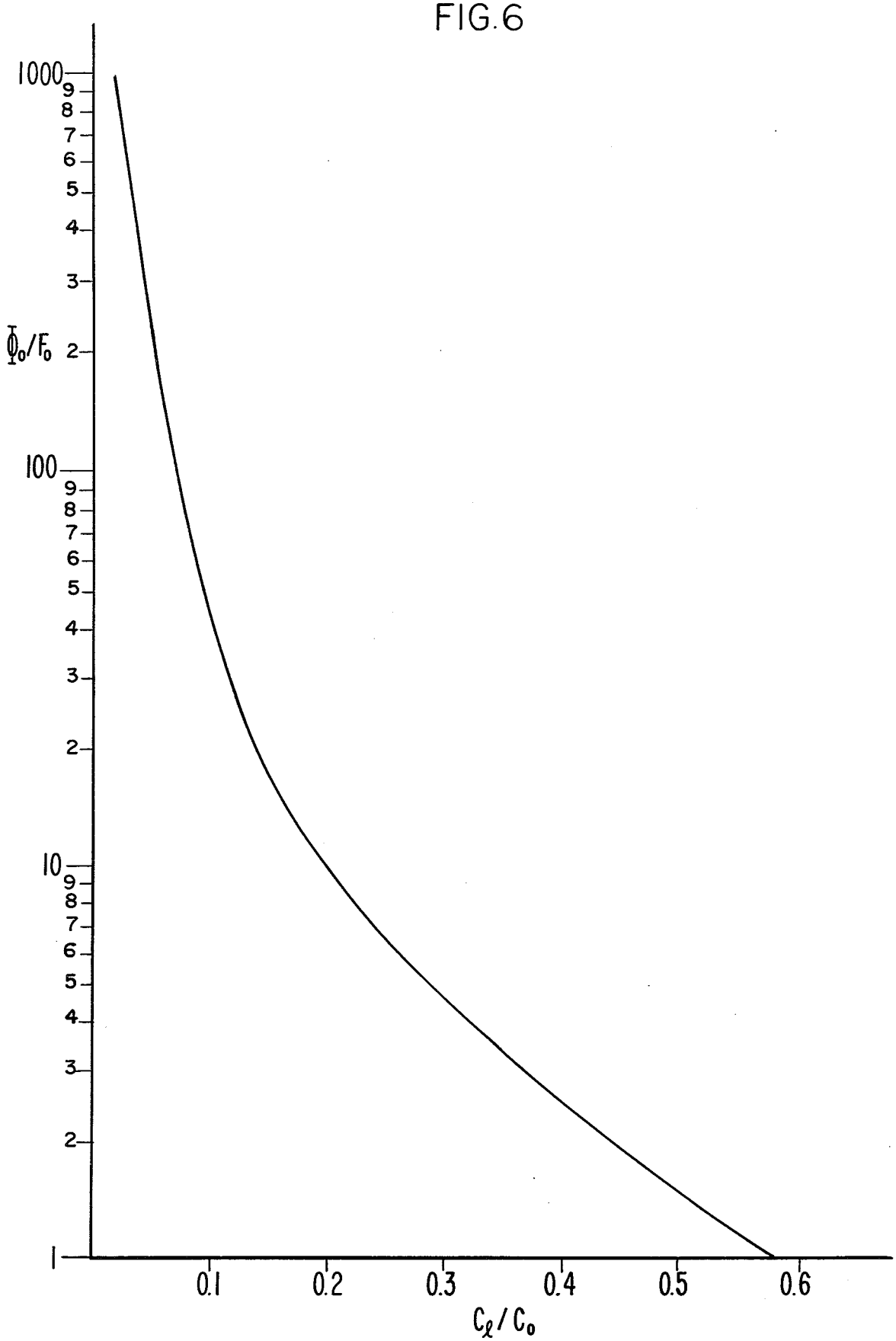

Turning now to the drawings in detail, which are examples of various osmotic delivery devices of the invention, and which examples are not to be considered as limiting, one example of an osmotic device is indicated in FIG. 1 by the numeral 10. In FIG. 1, device 10 comprises a body 11 that can be shaped, sized, adapted, and structured for easy placement an prolonged retention in a biological environment of use for the controlled delivery of a beneficial agent thereto. In FIG. 1, device 10 is seen comprising a wall 12, a passageway 13 through wall 12, and a dashed line 14 indicating where a layer of an insoluble compound contacts a layer of a soluble agent. The layered structure is discussed below in FIG. 2 and FIG. 3. Device 10 of FIG. 1 is designed for delivering an agent in a dilute solution. The term dilute means to decrease the amount of agent in solution by admixing fluid with the solution. A dilute solution is distinguished from a saturated solution, which latter solution is the most concentrated solution that can persist in the presence of an excess of the dissolved agent.

In FIG. 2, device 10 is seen in full opened-section. In FIG. 2, device 10 comprises a body 11 having an exterior wall 12 that surrounds and forms a compartment 17. Wall 12 is formed of a semipermeable polymer that is permeable to the passage of an exterior fluid and impermeable to the passage of compound, agents and drugs. A passageway 13, in wall 12, communicates with the exterior of device 10 and the boundary interface 18 defined by the inner surface of wall 12 and the layer of insoluble compound 15. Compound 15 is insoluble or practically insoluble in an exterior fluid imbibed into compartment 17. The fluid can be an aqueous fluid, such as water, or an aqueous like fluid such as a biological fluid present in the environment of use. Compartment 17 also contains a layer of a soluble agent 16, such as a drug. Agent 16 is distant from passageway 13 and the layer of agent 16 is not in contact with passageway 13. Agent 16 acts as an osmotically effective solute, it exhibits an osmotic pressure gradient across wall 12, and it imbibs exterior fluid into device 10 at a rate determined by these physical chemical properties.

In operation, the insoluble layer 15, and the soluble layer 16 operate together, as a unit to deliver agent 16 from device 10. That is, external fluid is imbibed into compartment 17 by agent layer 16 in a tendency towards osmotic equilibrium, at a rate determined by the permeability of wall 12, and the osmotic pressure gradient across wall 12, to dissolve agent 16 and form a saturated solution containing agent 16. This saturated solution moves under hydrostatic pressure through the interface defined by wall 12 and the layer of insoluble compound 15. The arrows on the inside of wall 12 of FIG. 3, indicate the flow of solution towards passageway 13. As the saturated solution moves through the interfaced area, it imbibs fluid from the exterior, as indicated by the arrows on the outside of wall 12 of FIG. 3, which fluid mixes with and dilutes the saturated solution. The saturated solution, as it moves along the interface, imbibs fluid at a rate proportional to the concentration of the agent at the interface, with the diluted solution continuously delivered through passageway 13, motivated by the corresponding imbibition of fluid.

System 10 of FIGS. 1, 2 and 3 can be made into many embodiments, including the presently preferred embodiment, an osmotic device for oral use. The device can be used for delivering a locally or a systemically acting therapeutic drug in the gastrointestinal tract over a prolonged period of time. The device can have conventional oral shapes and sizes such as round with a diameter of 3/16 inches to ½ inches, or it can be shaped like a capsule having a range of sizes from triple zero, and from 1 to 8. In these forms, device 10 can be adapted for administering drug to numerous animals, avians, fishes and reptiles. The term animal as used herein includes warm-blooded animals, which terms include mammals and humans.

FIG. 4 shows an osmotic device 10 designed for easy placement in a body passageway, such as the vagina, or the ano-rectal passages. Device 10 has an elongated, cylindrical, self-retaining shape with a rounded lead end 20 and a trailing base end 21, and it is equipped with manually controlled string 22 for easily removing device 10 from the body passage. Device 10 of FIG. 4 is structurally identical with device 10 of FIGS. 1, 2 and 3, as described above, and it operates in a like manner. Device 10 of FIG. 4 in one embodiment contains a drug designed for absorption by the vaginal mucosa or the rectal mucosa.

While FIGS. 1 through 4 are illustrative of various systems that can be made according to the invention, it is to be understood the systems made as devices are not to be construed as limiting the invention, as the devices can take a wide variety of shapes, sizes and forms for delivering drugs to different biological environments of use. For example, the devices include buccal, implant, eye, artificial gland, cervical, intrauterine, ear, nose, dermal, subcutaneous, and blood delivery devices. The devices can be used in hospitals, veterinary clinics, nursing homes, sickrooms, and the like.

DETAILED DESCRIPTION OF THE INVENTION

In accordance with the practice of this invention, it has now been found that osmotic delivery system 10 can be manufactured with a wall 12 formed of a material that does not adversely affect the insoluble compound, agent, drug, animal or other host. The wall forming material is a polymer that is permeable to the passage of an external fluid such as water and biological fluids, while remaining impermeable to compounds, agent-solutes, and drug-solutes. The selectively permeable materials forming semipermeable wall 12 are materials insoluble in body fluids and they are non-erodible, or they can be made to erode after a predetermined period, with the erosion occurring at the end of the drug delivery period. Typical materials for forming wall 12 include semipermeable polymers, also known to the art as osmosis membranes. The semipermeable polymers include cellulose acylate, cellulose diacylate, cellulose triacylate, cellulose ethers and cellulose esters. Typical semipermeable polymers include cellulose acetate, cellulose diacetate, cellulose triacetate, dimethyl cellulose acetate, cellulose acetate ethyl carbamate, and the like. Other semipermeable polymers include polyurethane, selectively permeable polymers formed by the coprecipitation of a polycation and a polyanion, polymers derived from polystyrene, and like polymers that are insoluble in aqueous and nonaqueous media. Generally, semipermeable polymers useful for forming wall 12 will have a fluid permeability of $10^{-5}$ to $10^{-1}$ (cc·mil/cm$^2$·h·r·atm) expressed as per atmosphere of hydrostatic or osmotic pressure difference across wall 12 as the temperature of use.

Those versed in the art to which this invention pertains can select a semipermeable polymer for forming wall 12 that is permeable to the passage of fluid by using the following criterions. The scientific criterions are: (a) the polymer possesses a high degree of substitution, for example, the polymer has undergone etherification or esterification particularly acylation towards or to completion with the polymer formed demonstrating increased resistance to the passage of fluid; (b) the polymer exhibits a flux decrease with increasing molecular size of the substituting group, such as an ether or ester group; (c) the polymer exhibits a flux decrease proportional to the increase in size of the substituent, for example, the decrease occurs as the number of carbon atoms increase in a hydrocarbon moiety such as alkyl or alkoxy moiety; (d) the polymer exhibits decreased flux with an increase in the degree of substitution of hydrophobic ether and larger hydrophobic ester groups, and (e) the polymer exhibits a flux decrease as the number of polar, ionic groups bonded to the polymer decreases.

The flux of a fluid, for example, the rate of water vapor transmission through various wall forming polymers also is ascertainable by using the procedure described in *Diffusion in Polymers*, pages 1 to 39, and then expressing the results of as WVTR, or water vapor transmission rate through a film of the polymer in grams/100 in $^2$/24 hr/one mil thick film. Known WVTR values can also be found in *Plastic Film Technology*, by Park, W. W. R., 1969, published by Van Nostrand-Reinhold Inc., and in *Diffusion in Polymers*, by Crank J., and Park G. S., pages 274 to 276, published by Academic Press. Typical values are set forth in Table 1 immediately below wherein the film is the wall forming polymer and WVTR is as defined.

TABLE 1

| Film | WVTR |
| --- | --- |
| Polyurethane | 30–50 |
| Cellulose acetate | 40–75 |
| Ethycellulose | 75 |
| Cellulose acetate butyrate | 50 |
| Polyvinylchloride, cast | 10–20 |
| Polyvinylchloride, extruded | 6–15 |
| Polycarbonate | 8 |
| Polyvinylfluoride | 3 |
| Ethylene vinyl acetate | 1–3 |
| Polyesters | 2 |
| Cellophane, polyethylene coated | >1.2 |
| Polyvinylidene fluoride | 1.0 |
| Polyethylene | 0.5–1.2 |
| Ethylene propylene copolymer | 0.8 |
| Polypropylene | 0.7 |
| Polyvinyl chloride, rigid | 0.7 |

Another criterion that can be used for measuring the fluid permeability of different polymeric films consists in using a standard osmosis cell. The measurement is carried out by using the osmosis cell and measuring the rate of fluid through a membrane made of wall forming polymer having a known composition and thickness. The flow rate is determined by measuring fluid transport from a first chamber containing a fluid free of agent through a polymer membrane that separates it from a second chamber housing a solution containing a known concentration of a drug or a solute that exhibits an osmotic pressure gradient across the membrane. The flow measurement is performed by adding to the first chamber the fluid and then adding to the second chamber, equipped with a stirring bar, the same fluid containing drug, and optionally containing an additional osmotic solute. The first chamber is connected through a conduit to a reservoir containing a supply of fluid, and the second chamber is connected to a vertically positioned tube of known diameter and calibrated with indicia that indicate the amount of fluid in the tube. In operation, fluid flows from the first chamber, through the membrane into the second chamber by osmosis causing the solution to rise over time, t, to give a volume displacement $\Delta V$, during a time interval, $\Delta t$. The volume, $\Delta V$, is read on the tube calibrated in cm$^3$, and the time interval, $\Delta t$, is, measured with a stopwatch. The value $k_o\pi$ in cm$^3$·mil/cm$^2$·hr for the membrane with permeability, $k_o$, for the drug solution with an osmotic pressure, $\pi$, is calculated from Equation (A), and wherein $A_o$ is the area of the membrane in the diffusion cell, and $h_o$ is the thickness of the membrane.

$$k_o\pi = (\Delta V/\Delta t)\cdot(h_o/A_o) \qquad (A)$$

Osmotic flow procedures are described in *J. App. Poly. Sci.*, Vol. 9, pages 1341 to 1362, 1965; and in *Yale J. Biol. Med.*, Vol. 42, pages 139 to 153, 1978.

The phrase a compound that is insoluble, or practically insoluble in aqueous fluids including water and biological fluids, comprise inorganic and organic compounds that exhibit a zero, or near zero osmotic pressure gradient across a semipermeable wall against an external fluid. These compounds do not substantially dissolve in, and they do not mix with the fluid. The layer consists essentially of an insoluble compound that maintains its structural integrity during the operational history of system 10. In FIG. 5, the insoluble layer is represented by dashed lines. Representative compounds include ferric acetate, ferric benzoate, aluminum linoleate, barium carbonate, bismuth pyrogallate, bismuth subcarbonate, bismuth subsalicylate, calcium carbonate, silicon tetraiodide, calcium linoleate, calcium resinate, ferric carbonate, cupric carbonate, barium fluorosilicate, barium sulfate, bismuth gallate, bismuth iodate, calcium aluminate, calcium tetraborate, calcium orthosilicate, ferric oxalate, lithium metasilicate, magnesium metasilicate, zinc ferrate and the like. The solubility of the compounds is set forth in *Handbook of Chemistry*, by Lange and Forker, 1952, published by Handbook Publishers, Inc., Sandusky, Ohio.

The term agent as used in this specification and the accompanying claims denotes pesticides, germicides, algicides, herbicides, rodenticides, fungicides, insecticides, anti-oxidants, plant growth promoters, plant growth inhibitors, disinfectants, catalysts, nutrients, drugs, vitamins, micro-organism attenuators, and other active agents that benefit man and the environment of use. In FIG. 5, the dots represent a layer of aqueous soluble agent 16, in contacting relation with a layer of aqueous insoluble compound 15. The amount of agent 16 in a layer is a unit amount for carrying out the desired program, usually 25 mg to 500 mg.

The term drug as used in this specification and the accompanying claims include any physiologically or pharmacologically active substance that produces a localized or systemic effect, or effects in animals, laboratory animals, mammals, humans, primates, farm animals, sport animals and zoo animals. The active drugs that can be delivered include inorganic and organic compounds without limitation, these materials act on the nervous system, they are hypnotics, sedatives, psychic energizers, tranquilizers, anti-convulsants, muscle relaxants, antiparkinson, antipyretics, anti-inflammatory, analgesics, anesthetics, muscle contractants, hormones, steroids, anti-microbials, sympathomimetric, cardiovascular, diuretics, neoplastics, hypoglycemics, amino acids, ophthalmic, vitamins, and the like. The beneficial drugs, and the amount to be delivered are known to the art in *Pharmaceutical Sciences,* by Remington, 14th Ed., 1970, published by Mack Publishing Co., Easton, Pa.; and in *The Pharmacological Basis of Therapeutics,* by Goodman and Gilman, 4th Ed., 1970, published by The MacMillian Company, London.

The expression passageway as used herein comprises means and methods suitable for releasing the drug from the device, and for transporting agent from the interface to the exterior of the device. The expression includes aperture, orifice, bore, or a passageway formed in situ by eroding a water soluble plug, such as a gelatin plug. A detailed description of osmotic passageway, that permits the device to function according to osmotic principles, and the maximum and minimum dimensions for a passageway are disclosed in U.S. Pat. No. 3,845,770 and 3,916,899.

The devices of the invention are manufactured by standard techniques. For example, in one embodiment agent housed in the compartment and a solvent are mixed into a solid, or semi-solid and pressed into a shaped form, by conventional methods to form a first layer of agent. Then, the insoluble compound housed in the compartment and a solvent are mixed into a solid, or semi-solid and pressed into a shaped form by conventional methods to yield the second layer of insoluble compound on the agent layer. The agent layer and the insoluble compound layer have identical shape for ease in manufacturing the device. The two layered structure can also be made by pressing under pressure the insoluble compound into a layer, and then pressing onto said layer the agent to form an insoluble compound-drug layered structure. The two layered structure can also be manufactured by forming each layer separately, and then placing them in contacting relation with each other. The compounds and drugs can be independently mixed with a binder for forming the layers. Other techniques that can be used include roll-milling, tableting and the like.

The wall forming material can be applied by molding, vacuum forming, spraying or by dipping the pressed shaped layers into the wall forming materials. In another embodiment, a wall can be cast, shaped to the desired dimensions that surrounds the compartment and the compartment filled with agent, then compound, closed and a passageway drilled through the wall to connect the insoluble compound interface with the exterior of the system.

In a presently preferred embodiment, the system is made by using an air suspension technique. This procedure consists in compressing agent, compressing insoluble compound, and then suspending and tumbling the layered structure in a wall forming composition until the semipermeable wall is applied around the layers. Next, after drying in a warm oven, a passageway is drilled through the wall to the interface at the inside of the wall and the compound layer. The air suspension procedure is described in U.S. Pat. No. 2,799,241; in *J. Am. Pharm. Assoc.,* Vol. 48, pages 451 to 459, 1959; and ibid., Vol. 49, pages 82 to 84, 1960. Other wall forming techniques such as pan coating can be used in which materials are deposited by successive spraying of the polymer solution on the agent, drug, or compound, accompanied by tumbling in a rotating pan. Other standard manufacturing procedures are described in *Modern Plastics Encyclopedia,* Vol. 46, pages 62 to 70, 1969; and in *Pharmaceutical Sciences,* by Remington, 14th Ed., pages 1626 to 1678, 1970, published by Mack Publishing Company, Easton, Pa. Generally, the wall will be about 2 to 10 mils thick. Of course, thinner and thicker walls are within the scope of the invention.

Exemplary solvents suitable for manufacturing the walls include inert inorganic and organic solvents that do not adversely harm the wall forming materials, the drug, the agent, and the final device. The solvents broadly include aqueous solvents, alcohols, ketones, esters, ethers, aliphatic hydrocarbons, halogenated solvents, cycloaliphatic aromatics, heterocyclic solvents, and mixtures thereof. Typical solvents include acetate, ethyl acetate, methyl isobutyl ketone, n-hexane, ethylene glycol monoethyl acetate, carbon tetrachloride, methylene chloride, ethylene dichloride, propylene dichloride, cyclohexane, mixtures such as acetone and water, acetone and methanol, acetone and ethyl alcohol, methylene dichloride and methanol, ethylene dichloride and methanol, and mixtures thereof.

DESCRIPTION OF EXAMPLES OF THE INVENTION

The following examples are merely illustrative of the present invention, and they should not be considered as limiting the scope of the invention in any way, as these examples and other equivalents thereof will become more apparent to those versed in the art in the light of the present disclosure, the drawings and the accompanying claims.

EXAMPLE 1

An osmotic delivery system for delivering a beneficial agent at an osmotically controlled rate is illustrated by FIGS. 1 through 3, operates as follows to deliver agent to the environment of use. The part of the system that contains the active agent imbibes fluid to produce a solution at concentration $C_o$ in the agent compartment. Through continuous imbibition of fluid this solution is then pumped at a volume flow $dV/dt = F_o$ into the diluting interface. In the Figures, when the total system is exposed to a fluid environment of use, for example water, where the activity of water is higher than in the system, water will be imbibed through the semipermeable wall into the interface defined by the boundary between the inside of the wall and the surface of the insoluble layer faced with the wall. The water imbibed into the interface dilutes the concentration of the solution moving through the interface, in the direction seen in FIG. 3, by the arrow heads, and out through the passageway. The interface along the semipermeable wall acts as a dilutor, the dilution will be proportional to the amount of water imbibed into the interface. The concentration Cl of solution delivered from the system is calculated here as a function of the characteristics of the systems assuming a constant activity of water surrounding the system at steady state. It is assumed this activity is zero.

Thus, in any length $\Delta_x$ in the interface, the volume inflow is $F_x$, the outflow is $F_{x+\Delta_x}$, and the volume inflow across the wall is $F_c \cdot \Delta_x$, when $F_c$ is the inflow per unit length of interface. This is expressed by equation 1.

$$F_c = K_t \pi \cdot (6.28 r/h) \quad (1)$$

Wherein r is the radius of the wall, $K_t$ is the permeability of the wall to fluid, $\pi$ is the osmotic pressure in section $\Delta_x$ of the interface, and h is the wall thickness. The volume flux is defined as the volume transported per unit area and time. Then, from this it follows, the flux increase in the interface is equal to that expressed in equation 2.

$$F_{x+\Delta x} - F_x = F_c \cdot \Delta_x \quad (2)$$

with the flux imbibed, equation 2, which in the limit of a small $\Delta_x$ results in equation 3.

$$(dF_x/dx) = F_c \quad (3)$$

The Flux $F_x$ at any distance x in the interface is obtained by integrating equation 3; however $F_c$ is also a function of x as given by equation (1) and must be substituted.

At steady state, $\pi_o$ and $C_o$ are the osmotic pressure and the concentration of agent solute hydrostatically pumped from the system at x=o, and they relate to $\pi$ and $C_x$ as given by equation 4, $$(\pi/\pi) = (C_x/C_o) \quad (4)$$

Substituting equation 4 into equation 1, gives $F_c$ as expressed by equation 5.

$$F_c = a \cdot c_x \quad (5)$$

wherein a is a constant as defined by equation 6.

$$a = 6.28 \cdot \frac{r}{h} \cdot k_t \cdot \frac{\pi_o}{C_o} \quad (6)$$

Equation 3 and equation 5 combined result in equation 7, wherein C must be further expressed as a function of X or $F_x$.

$$\frac{dF_x}{dx} = C_x \cdot a \quad (7)$$

Although a volume of fluid is continuously imbibed through the semipermeable wall into the interface, the mass delivery rate of agent is constant as expressed by equation 8.

$$\frac{dm}{dt} = F_o \cdot C_o \cdot = F_x \cdot C_x = F_l \cdot C_l \quad (8)$$

And, on substituting equation 8 into equation 7, the equation can be integrated and results in equation 9, and then 10.

$$\int_o^{F_x} F_x \cdot dF_x = \int_o^x F_o \cdot C_o) dx \quad (9)$$

$$F_x^2 = F_o^2 + 2aF_o C_o /c \quad (10)$$

For x=1 it follows that Fl is given by equation 11.

$$F_l^2 = F_o^2 + 2a \cdot F_o \cdot C_o \cdot l \quad (11)$$

Equation 12 follows from equation 8.

$$Cl = \frac{F_o \cdot C_o}{F} \quad (12)$$

The concentration at the exit Cl at the junction of the interface length follows from equation 11 and equation 12, and is given by equation 13.

$$Cl = \frac{F_o \cdot C_o}{\cdot F_o \left(1 + 2 \frac{C_o \cdot a}{F_o} \cdot l\right)^{\frac{1}{2}}} \quad (13)$$

The volume flow $\phi_o$ can be defined as the flux imbibed into the interface filled with a solution with uniform concentration $C_o$ at osmotic pressure $\pi_o$ according to equation 14. The volume flow $\phi_o$ is a number that characterises the dilution capacity of the dilution member.

$$\phi_o = k \pi_o 6.28 \frac{r}{h} \cdot l = a \cdot C_o \cdot l \quad (14)$$

From this, it follows that equations 13 and equation 14 reduce then to equation 15.

$$\frac{Cl}{C_o} = \frac{1}{\left(1 + 2 \frac{\phi_o}{F_o}\right)^{\frac{1}{2}}}$$

When the dilution members, the interface, is made of the same material as the system, and of the same size, $\phi_o = F_o$, and $Cl = C_o \sqrt{3}$, the exit passageway concentration is reduced by $\sqrt{3}$. In Table 2, the dilution values $Cl/C_o$, as a function of the design parameter $\phi_o/F_o$ are listed, which values are further represented in FIG. 6.

TABLE 2

DILUTION FACTOR $Cl/C_o$ AS A FUNCTION OF THE PUMPING RATIO $\phi_o/F_o$

| $Cl/C_o$ | $\phi_o/F_o$ |
|---|---|
| 0.58 | 1 |
| 0.3 | 5 |
| 0.2 | 10 |
| 0.07 | 100 |
| 0.02 | 1000 | and, $$\frac{\phi_o}{F_o} = k_t \frac{A_t}{h_t} / k_o \frac{A_o}{h_o} \quad (16)$$

wherein t is the subscript for the interface and o is for the system, and A, represents the area. It is clear that if the system and the interface are made from the same material, $k_t = k_o$, and if the thickness of the semipermeable wall is the same as the thickness of the interface, then $h_t = h_o$, and $\phi_o/F_o$ is equal to the ratio of the areas of the interface and the system respectively. In FIG. 6, the numbers on the x axis indicate ratio of the concentration of the agent in solution at the exit passageway to the concentration of the agent in solution at the exit passageway to the concentration at the start of the interface, and, the y axis is the ratio of volume flux imbibed into the interface filled with a solution concentration $C_o$, to the flux into osmotic compartment filled with the same concentration $C_o$. FIG. 6 is a semi-log plot of the log of the flow ratio vs the concentration ratio.

EXAMPLE 2

As osmotic device for delivering potassium chloride at an osmotically controlled rate is made as follows: first, 500 mg of commercially available, dry powdered potassium chloride is mixed with 2 mg of the water soluble binder gelatin and the mixture compressed by standard technique in a ⅜ inch cavity with a punch to form a layer of agent. Next, 400 mg of the water insoluble compound calcium carbonate stained with a non-toxic blue dye is added to the cavity and the compound compressed under pressure to form a layer of insoluble compound. The two layered structure is then coated with a 5.5 mil thick wall of semipermeable polymer, cellulose acetate having an acetyl content of 38.3%. The wall is formed from a 80 to 20 parts by weight mixed methylene chloride-methanol solvent. A Wurster air suspension machine is used to form the wall. The solvent is evaporated in an oven at 50° C. for 48 hours, and after cooling to room temperature, a 7.5 mil passageway is laser drilled through the wall, using the dye as a guide. The passageway connects the exterior of the device with the interface for releasing diluted solution to the environment of use.

EXAMPLE 3

The procedure of Example 2 is repeated with the semipermeable wall in this example formed of cellulose acetate having an acetyl content of 32%. A 5% polymer solution in dioxane is used to form the wall, which has a thickness of about 7 mils. After drying, a passageway is laser drilled through the semipermeable wall connecting the exterior of the device with the interface boundary defined by the inside surface of the wall and the surface of the insoluble compound facing the wall.

EXAMPLE 4

A non-stirring rate dependent osmotic device that releases a diluted drug solution independent of the pH of the environment of use is manufactured as follows: first, 150 mg of the diuretic ethacrynate sodium having a solubility in water of 25° C. up to 9%, is compressed into a solid mass in a commercially available Manesty tableting machine to a Stoke's hardness of 8 kg.

Next, 350 mg of ferric acetate which is practically insoluble in water, is pressed in the Manesty machine to a Stoke's hardness of 10 kg. The pressed compound has a shape identical to the shape of the pressed drug. Then, a small drop of liquid cellulose acetate is placed on the center of the drug, and this surface is placed against the corresponding surface of the insoluble compound. The two united masses are then coated in an air suspension machine with a wall of semipermeable cellulose acetate to a thickness of 10 mil. The wall is formed from a 4% solution consisting essentially of cellulose acetate having an acetyl content of 32%. The solution is made by dissolving 155 g of cellulose acetate in a solvent consisting essentially of 3300 ml of acetone and 428 ml of water. After drying, as osmotic passageway having a diameter of 10 mils is drilled through the wall to the interface of the insoluble compound. The device delivers diluted drug solution over a prolonged period of time.

EXAMPLE 5

A two layered structure for housing in the compartment of an osmotic system is manufactured by forming a first layer under pressure a layer consisting essentially of a member selected from the group consisting essentially of ferric acetate, ferric benzoate, alluminum linoleate, barium carbonate, bismuth pyrogallate, bismuth subcarbonate, bismuth subsalicylate, calcium carbonate, silicon tetraiodide, calcium linoleate, calcium resinate, ferric carbonate, cupric carbonate, barium fluorosilicate, bismuth gallate, bismuth iodate, calcium aluminate, calcium tetraborate, calcium orthosilicate, ferric oxalate, lithium metasilicate, magnesium metasilicate and zinc ferrate, which layer is in intimate contacting with a layer formed of a member selected from the group consisting essentially of a hypnotic, sedative, psychic energizer, nervous system psychic energizer, tranquilizer, anti-convulsant, muscle relaxant, antiparkinson, antipyretic, anti-inflammatory, analgesic, anesthetic, muscle contractant, hormone, steroid, antimicrobial, sympathomimetic, cardiovascular, diuretic, hypoglycemic, and ophthalmic drug. In FIG. 5, the insoluble compound is represented by dashes 15, and the drugs by dots 16. The amount of compound or drug in a layer usually corresponds to the amount housed in the device for carrying out a therapeutic program, usually 5 mg to 800 mg, and more preferably 25 mg to 500 mg per layer of each. The layer also embraces a design that resembles the design of the device and they have a thickness of about 1 mm to 7 mm each, with a preferred thickness of 2 mm to 5 mm thick each.

The novel system of this invention uses embodiments for obtaining the delivery of agents at reduced concentrations to the environment of use, while simultaneously maintaining the benefits of the agent. While there are described and pointed out features of the invention as applied to presently preferred embodiments, those skilled in the art will appreciate that various changes, modifications, additions, and omissions in the devices illustrated and described can be made without departing from the spirit of the invention.

We claim:

1. An osmotic system for the controlled delivery of a beneficial agent to an environment of use, comprising:
  (a) a wall formed of a semipermeable material permeable to the passage of an exterior fluid, and substantially impermeable to the passage of agents and compounds, the wall surrounding and forming;
  (b) a compartment containing a layer of an agent that is soluble in the exterior fluid and exhibits an osmotic pressure gradient across the wall against the fluid, and a layer of a compound that is substantially insoluble in the exterior fluid; and,
  (c) a passageway through the wall communicating with the interface defined by the wall's inside surface and the surface of the layer of the insoluble compound.

2. The osmotic system for the controlled delivery of a beneficial agent according to claim 1 wherein the compound insoluble in the exterior fluid exhibits a substantially zero osmotic pressure gradient across the wall against the exterior fluid.

3. The osmotic system for the controlled delivery of the beneficial agent according to claim 1 wherein in operation when the system is in a fluid environment of use, fluid from the environment is imbibed through the wall by the agent in a tendency towards osmotic equilibrium, at a rate determined by the permeability of the wall and the osmotic pressure gradient across the wall to form a solution containing agent that flows under hydrostatic pressure through the interface and imbibs fluid through the wall, which imbibed fluid dilutes the solution, with the diluted solution delivered through the passageway from the interface to the exterior of the system.

4. The osmotic system for the controlled delivery of the beneficial agent according to claim 1 wherein the system is manufactured as a device shaped, sized and adapted as a dosage form for delivering an agent to the gastrointestinal tract, and wherein the agent is a drug.

5. The osmotic system for the controlled delivery of a beneficial agent according to claim 1 wherein the system is manufactured as a device sized, shaped and adapted as a dosage form for delivering the agent to the ano-rectal canal, and wherein the agent is a drug.

6. The osmotic system for delivering the beneficial agent according to claim 1 wherein the agent is a drug.

7. The osmotic system for delivering the beneficial agent according to claim 1 wherein the agent is a drug selected from the group consisting of an anticonvulsant, antiparkinson, analgesic, anti-inflammatory, anesthetic, hormonal, contraceptive, sympathomimetic, diuretic, ophthalmic, nervous system, sedative, tranquilizer, anti-infective and hypoglycemic drugs.

8. The osmotic system for delivering the beneficial agent according to claim 1 wherein the semipermeable wall is formed of a member selected from the group consisting of cellulose acylate, cellulose diacylate, cellulose triacylate, cellulose ether, cellulose ester and mixtures thereof.

9. The osmotic system for delivering the beneficial agent according to claim 1 wherein the insoluble compound is a member selected from the group consisting of ferric acetate, ferric benzoate, aluminum linoleate, barium carbonate, bismuth pyrogallate, bismuth subcarbonate, barium sulfate, bismuth subsalicylate, calcium carbonate, silicon tetraiodide, calcium linoleate, calcium resinate, ferric carbonate, cupric carbonate, barium fluorosilicate, bismuth gallate, bismuth iodate, calcium aluminate, calcium tetraborate, calcium orthosilicate, ferric oxalate, lithium metasilicate, magnesium metasilicate and zinc ferrate.

10. The osmotic system for delivering the beneficial agent according to claim 1 wherein the exterior fluid is a member selected from the group consisting of water and biological fluids.

11. A two layered structure comprising a layer formed of a compound substantially insoluble in an aqueous fluid, said compound a member selected from the group consisting essentially of ferric acetate, ferric benzoate, aluminum linoleate, barium carbonate, barium sulfate, bismuth pyrogallate, subcarbonate, bismuth subsalicylate, calcium carbonate, silicon tetraiodide, calcium linoleate, calcium resinate, ferric carbonate, cupric carbonate, barium fluorosilicate, bismuth gallate, bismuth iodate, calcium aluminate, calcium tetraborate, calcium orthosilicate, ferric oxalate, lithium metasilicate, magnesium metasilicate and zinc ferrate, which layer is in contact with a layer formed of an aqueous soluble drug, the drug a member selected from the group consisting essentially of nervous system, hypnotic, sedative, psychic energizers, tranquilizers, anticonvulsant, muscle relaxants, antiparkinson, antipyretic, anti-inflammatory, analgesic, anesthetic, muscle contractant, diuretic, neoplastic, hypoglycemics, ophthalmic drugs.

12. The osmotic system for the controlled delivery of the beneficial agent according to claim 1 wherein the environment of use is a human.

13. A two layered structure according to claim 10 wherein the layers are 1 mm to 7 mm thick.

14. A two layered structure according to claim 10 wherein the layer of insoluble compound consists essentially of 25 mg to 500 mg of a compound that is substantially insoluble an aqueous fluid, which fluid is a biological fluid.

15. A two layered structure according to claim 10 wherein the layer of aqueous soluble drug consists essentially of 25 mg to 500 mg of drug, and wherein the aqueous fluid is a biological fluid.

* * * * *